United States Patent [19]

Lipscomb

[11] Patent Number: 5,216,926
[45] Date of Patent: Jun. 8, 1993

[54] CLOSED AND OPEN TUBE SAMPLING APPARATUS

[75] Inventor: James H. Lipscomb, Wilmington, Del.

[73] Assignee: E. I. Du Pont de Nemours and Company, Wilmington, Del.

[21] Appl. No.: 924,636

[22] Filed: Aug. 5, 1992

Related U.S. Application Data

[63] Continuation of Ser. No. 509,987, Apr. 18, 1990, abandoned.

[51] Int. Cl.⁵ .......................................... G01N 35/06
[52] U.S. Cl. ........................ 73/864.25; 73/863.01; 73/863.85; 73/864.22
[58] Field of Search .......... 73/863.01, 863.02, 863.03, 73/863.83, 863.84, 863.85, 864.21–864.25, 864.73, 864.74, 864.34, 864.35; 422/63–67; 436/43, 45, 47–51, 54

[56] References Cited

U.S. PATENT DOCUMENTS

| | | | |
|---|---|---|---|
| 3,487,696 | 1/1970 | Hoffa | 73/864.25 |
| 3,719,086 | 3/1973 | Bannister et al. | 73/864.22 |
| 3,728,079 | 4/1973 | Moran | 73/864.25 X |
| 3,756,459 | 9/1973 | Bannister et al. | 222/1 |
| 3,759,667 | 9/1973 | Bannister et al. | 73/864.22 |
| 3,872,730 | 3/1975 | Ringrose et al. | 73/864.23 |
| 3,894,438 | 7/1975 | Ginsberg | 73/863.01 |
| 3,912,452 | 10/1975 | Sodickson et al. | 436/50 |
| 4,065,973 | 1/1978 | Gordon | 73/864.25 |
| 4,217,780 | 8/1980 | O'Connell et al. | 73/864.25 X |
| 4,311,484 | 1/1982 | Fosslien | 73/864.21 |
| 4,539,855 | 9/1985 | Jacobs | 73/864.25 |
| 4,581,583 | 4/1986 | Van Vliet et al. | 73/863.01 X |
| 4,756,201 | 7/1988 | Uffenheimer | 73/864.83 |
| 4,757,437 | 7/1988 | Nishimura | 73/863.01 X |
| 4,799,393 | 1/1989 | Uffenheimer | 73/864.22 |
| 4,811,611 | 3/1989 | Uffenheimer | 73/864.22 |
| 4,815,325 | 3/1989 | Averette | 73/864.21 |
| 4,841,786 | 6/1989 | Schulz | 73/864.25 |
| 5,045,286 | 9/1991 | Kitajima et al. | 73/864.24 X |
| 5,055,408 | 10/1991 | Higo et al. | 436/48 |
| 5,132,088 | 7/1992 | Wakatake | 73/864.21 X |

FOREIGN PATENT DOCUMENTS

| | | |
|---|---|---|
| A16756/88 | 12/1988 | Australia . |
| 0083474 | 7/1983 | European Pat. Off. . |
| 0212628 | 3/1987 | European Pat. Off. . |
| 8912829 | 12/1989 | PCT Int'l Appl. . |

*Primary Examiner*—Tom Noland

[57] ABSTRACT

An automatic sampling apparatus is constructed to use bang-bang fluid driven actuators whose control system is modified to permit accurate positioning over its range of motion. The actuators are positioned to aspirate liquid contents held within stoppered sample containers and equilibrate pressure in the sample containers to atmospheric prior to aspiration.

6 Claims, 3 Drawing Sheets

CLOSED AND OPEN TUBE SAMPLING APPARATUS

This is a continuation of application Ser. No. 07/509,987 filed Apr. 18, 1990, now abandoned.

FIELD OF THE INVENTION

This invention relates to an automatic sampling apparatus which is capable of automatically sampling the contents of open as well as closed sample containers.

BACKGROUND OF THE INVENTION

In the analytical and diagnostic fields there is a need to aspirate the contents of plural sample containers for analysis. While many samples are non-toxic and non-hazardous and hence may be held in open containers, it is often desirable to store samples in tubes which are closed, i.e. they have a cap over their top. The cap is used from the standpoint of safety to avoid exposing operators to contact with potentially hazardous serum and other materials. Often the samples are stored in a simple closed container of the type sold under the tradename Vacutainer® which finds wide usage in the blood industry.

As the trend towards automation of the sampling continues, it is necessary to introduce a probe through the rubber stopper or cap of the sample container for the purpose of aspirating a sample therefrom. In the past, such automation has been achieved using robotic systems of the type that provide movement in the X, Y, and Z directions. Such systems often use stepping motors as their prime movers. While imminently satisfactory and precise and accurate, such systems often encounter difficulties when the container cap is formed of a heavier, thicker or more resistant material such as rubber is encountered. This is due to the low torque provided by most stepping motors. Thus while quite satisfactory for sampling open tubes or open tubes stoppered with a material which is easily punctured, stepping motors are not satisfactory for use when use of containers stoppered with such heavy materials is necessary.

Typical of the open tube samplers that are available are those described in U.S. Pat. Nos. 3,719,086, 3,756,459, 3,759,667, 3,912,452, and 4,065,973.

A second problem encountered with the use of stoppered containers is that they often are evacuated as in the case of the Vacutainer® container due to the presence of a vacuum within the container. This renders it more difficult to accurately sample a fixed volume from the tube due to negative air pressure. Thirdly, it is desirable to present stoppered as well as unstoppered tubes on the same sample carrier.

One sampler which purports to alleviate some of these difficulties is that described in U.S. Pat. No. 4,811,611 issued to Uffenheimer. The Uffenheimer apparatus is capable of aspirating sample from both closed and open tubes. A pressure equilibration chamber prevents vacuum buildup in the closed tube sampler to ensure the supply of consistent sample quantities therefrom. Unfortunately the Uffenheimer apparatus requires that the closed tube be positioned in a separate portion of the sampler upside down. This renders automation difficult since open tubes must be positioned apart from and differently than the closed tubes. Also, if automating apparatus is to be used to position the sample containers and the aspirating apparatus must be used for the open and closed tubes respectively. Additional Uffenheimer patents of interest are U.S. Pat. No. 4,799,393 and U.S. Pat. No. 4,756,201.

U.S. Pat. No. 4,815,325 (Averatte) discloses a capillary fluid injector capable of sampling from septum covered vials. Utilizes air cylinders for probe motion but, each air cylinder is capable of stopping at the end of travel only. Venting of vial is through co-axial needle. Does not incorporate level sensing and aspiration probe always goes to a fixed depth in vial.

U.S. Pat. No. 4,311,484 (Fosslien) discloses automated sampling system for closed tubes only in which the tube to be sampled is held horizontally. Venting is accomplished by venting the probe to atmosphere. Due to the horizontal tube position venting will create bubbles in the sample which can affect aspiration. No level sensing is incorporated and the probe always enters to a fixed depth. Actuation of the probe into the tube is by motorized cam drive.

U.S. Pat. No. 3,872,730 (Ringrose et al.) discloses sampling system for closed tubes only in which the tube to be sampled is held horizontally and must be manually inserted. Venting is accomplished by a second probe which is open to atmosphere. Due to the horizontal tube position venting will create bubbles in the sample which can affect aspiration. No level sensing is incorporated and the probe always enters to a fixed depth. Actuation of the probe into the tube is manual.

AU-A-16756/88 (Mawhirt et al.) discloses an automated sampling system for closed tubes only in which the tube to be sampled is inverted. Venting is accomplished by venting the probe to atmosphere. Due to the vertical tube position venting will create bubbles in the sample which can affect aspiration. No level sensing is incorporated and the probe always enters to a fixed depth. Actuation of the probe into the tube is by air cylinder.

SUMMARY OF THE INVENTION

The apparatus of this invention overcomes many of the problems encountered in prior art automatic samplers and permitting open tube as well as closed tube sampling particularly when the tubes are positioned on the same rotary tray or carousel. Pressure within the closed tube is compensated. Adequate force is provided to permit the sampling probe to penetrate the cap of the closed tube. The subject apparatus of this invention has a sample carrier adapted to move a plurality of sample containers in a sampling position, a lateral translator located to have a path of movement over the sampling positions, a vertical translator mounted to be positioned by the horizontal translator, a sampling probe adapted to be positioned vertically by the vertical translator into and out of the sample containers, a liquid pump connected to the probe to aspirate sample from the sample containers, and controller means to actuate the translators and pump to effect such aspirators. The apparatus of this invention improves the sampling apparatus by the use of pneumatic translators, upright sample containers wherein at least one sample container is closed. This sampling apparatus includes a retaining bracket for the sample containers positioned to limit their upward movement during probe withdrawal from the container.

A transfer vessel is located along the path of movement of the lateral translator and the controller means operates the lateral translator to position the probe over the transfer vessel, the vertical translator and pump operating to discharge aspirated sample into the transfer vessel. A wash receptacle may be located along the path of the movement of the lateral translator, the controller means operating the lateral translator to position the probe over the wash receptacle. The apparatus also includes a source of wash liquid, the pump being coupled to the source, and includes a vertical translator and pump operating to discharge wash liquid into the receptacle and to dip the probe into the receptacle to wash the probe.

The apparatus also is constructed so that the pump is connected by a conduit to the probe and includes a valve positioned in the conduit and responsive to the controller veins to opening the conduit to atmospheric pressure immediately prior to sample laseration, to equilibrate the pressure in closed sample containers.

Thus constructed the automatic sampler provides more convenient and flexible sample loading onto a sample wheel without reconfiguring the hardware, software or switch selective valves to accommodate either open or closed sample tubes. Both types of containers, open as well as closed, by not requiring removal of the caps from the sample containers, laboratory productivity and particularly laboratory safety due to the removal of the hazardous material problem is substantially reduced.

DESCRIPTION OF THE DRAWINGS

The invention may be better understood by the following detailed description when taken together with the accompanying drawings in which.

DETAILED DESCRIPTION OF THE PREFERRED EMBODIMENT

Figure 1:
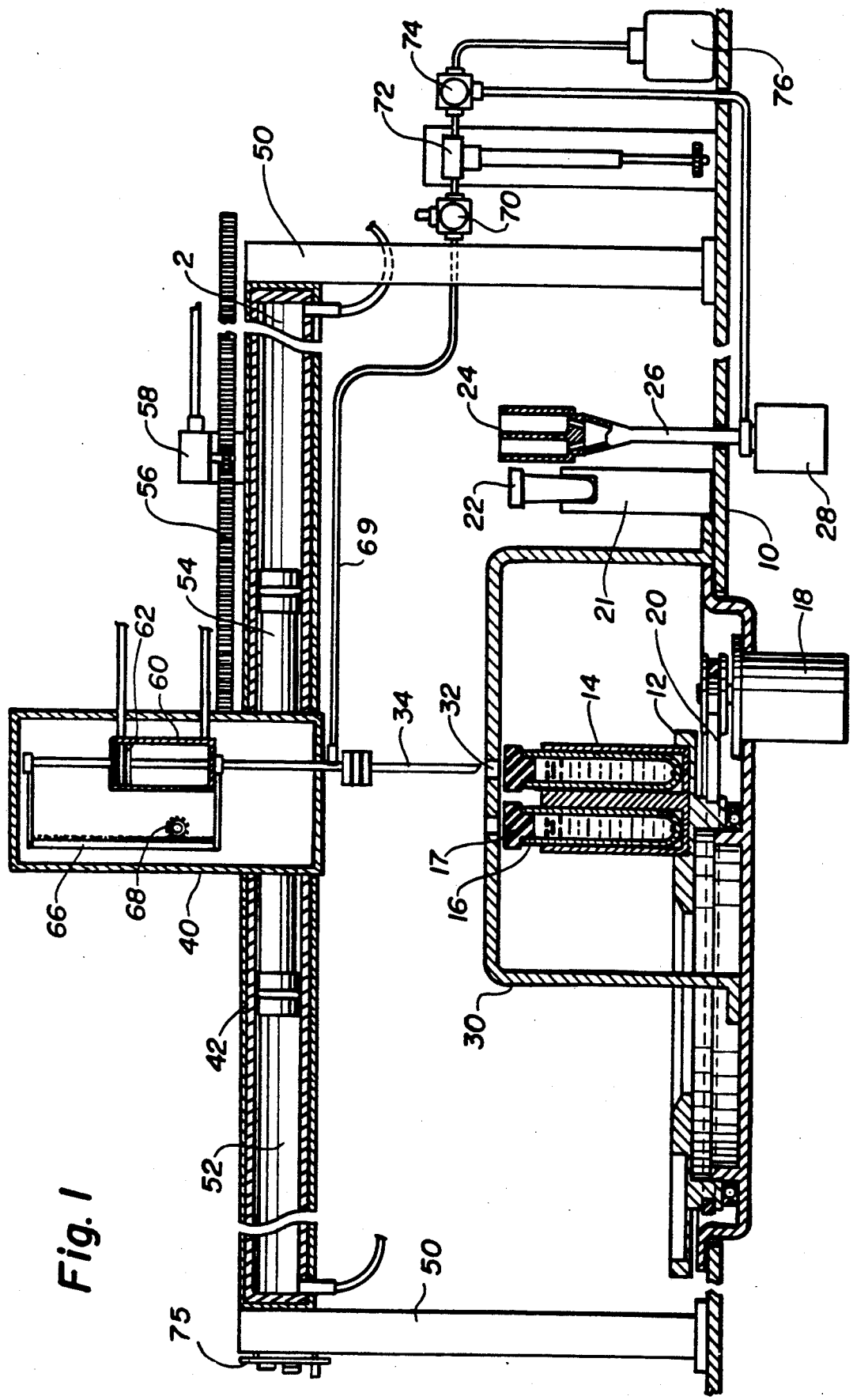
FIG. 1 is a diagrammatic view of an automatic sampling apparatus constructed in accordance with this invention.
Figure 2:
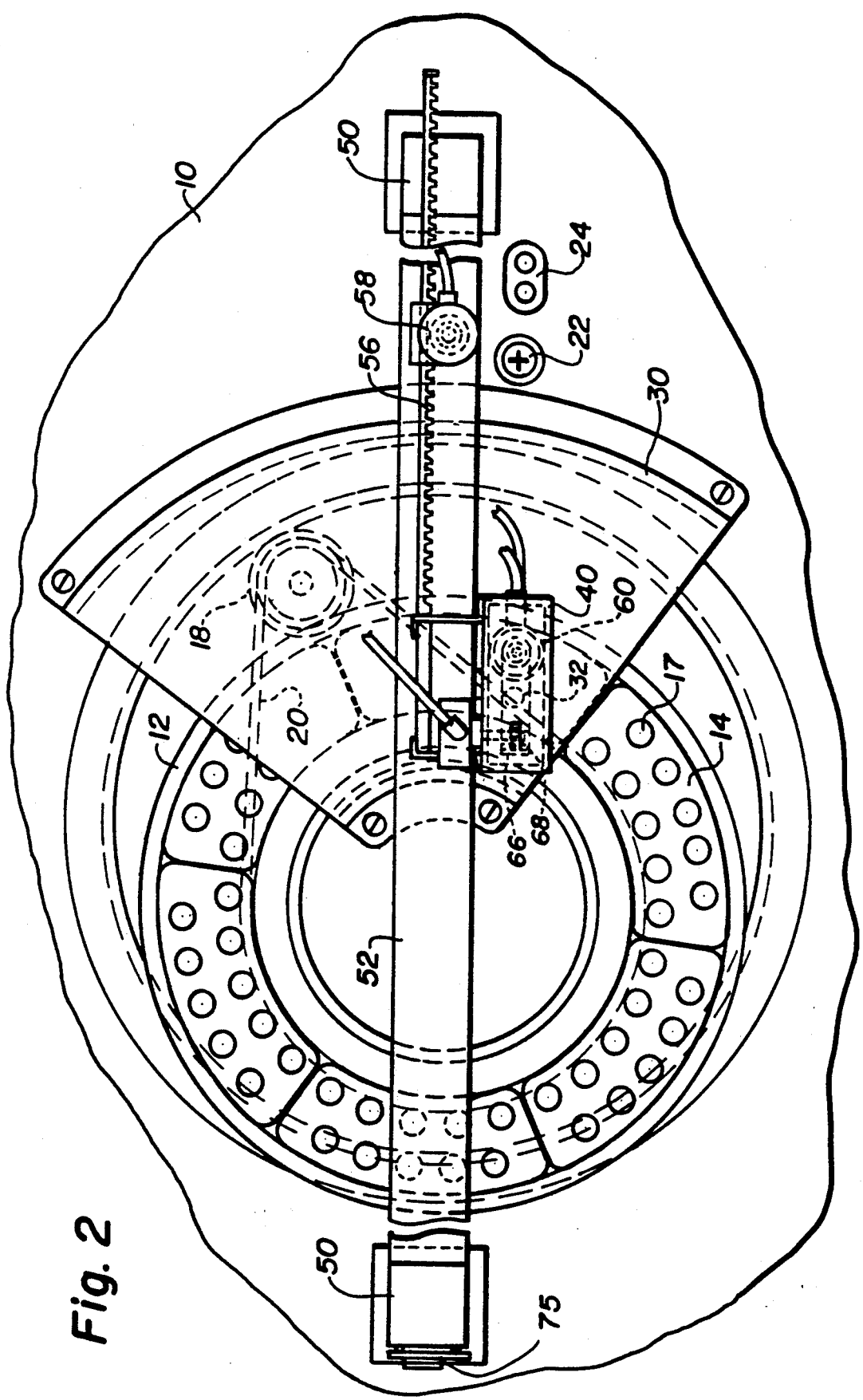
FIG. 2 is a plan view of the closed container sampling apparatus shown in FIG. 1.

The sampling apparatus which is capable of sampling either open or closed sample containers with equally facility is best seen with reference to FIGS. 1 and 2. In FIG. 1 the sampler has a base member 10. A sample carousel or wheel 12 is mounted on the base member. The sample wheel 12 typically rotates in one direction only and has a plurality of carriers 14 adapted to hold plural sample containers 16 of either the open and/or closed end variety. The sample containers of the closed end variety may typically be those which are sold for the purpose of collecting blood samples under the tradenames of Vacutainer ®, Venor Jet, or others. The sample wheel 12 is driven by a motor 18 through a pulley 20 all of conventional design.

Also mounted on the base 10 is a pedestal 21 adapted to hold a transfer vessel 22. A probe wash station 24 is positioned adjacent to the transfer vessel 22 and the two are in general alignment along a straight line intersecting the sampling location for the sample container 16. The wash station 24 has a drain pipe 26 which ends in a waste container 28. A retainer 30 is positioned over the sample wheel 12 and is positioned so as to prevent the upward movement of a sample container 16 once they are positioned under the retainer 30. The retainer 30 as may be best seen in FIG. 2 may be arcuate in shape. Holes 32 are formed the retainer 30 above the sampling location of the sample containers so as to admit the entry therethrough of a needle probe 34 which, as will be described, is used to extract sample and penetrate the stopper 17, if there be one.

The probe 34 is mounted on X and Z (horizontal and vertical) translators 40 and 42, respectively. These translators operate to position the probe 34 horizontally first above the sample containers 16 then over the transfer vessel 22 and finally over the wash station 24. The XZ translator operates to move the probe 34 vertically into and out of the sample container 16, the transfer vessel 22, if desired, and finally the wash station 24.

The horizontal translator 42 is mounted on stanchions 50 which in turn are mounted on the base 10 and mounts the Z-axis translation 40. The translator 42 includes a bang-bang fluid motor 52 has a piston 54 that slides back and forth therein as will be described. The fluid motor may be pneumatic or hydraulic, the former being preferred.

The piston 54 is in turn connected to position a Z-axis translator 40 and also drives a pinion rack 56 which in turn drives an X-axis encoder 58.

The Z-axis translator is also a bang-bang fluid motor 60, and includes a piston 62. A Z-axis pinion drive rack 66 is attached to the shaft driven by the piston 62 and engages a rotary encoder 68. The piston 62 is connected to drive the probe 34 in a vertical direction. The probe is connected to receive fluid through a tube 69 which is connected through a 2-way valve 70 to a pump 72. The pump 72 in turn is connected through a second 2-way valve 74 to a supply of wash buffer 76. The second outlet of the first valve 70 is connected to a vent to atmosphere. The pressure lines for the X and Z axis translators 42 and 40 are connected to suitable servo valves which are seen most clearly in FIG. 3. Before going to FIG. 3, it should be stated that the structure of the automatic sampling apparatus is controlled by a controller 80 which is shown schematically and will be described with particular reference to FIG. 3. The control system of FIG. 3 in addition to operating the translators 40 and 42 receives information from the encoders 58 and 68 and controls the operation of the respective servo valves 90 (FIG. 3) pumps and the liquid valves 70 and 74. The liquid valves 70 and 74 may be conventional solenoid operated valves. A level sensor 75, of conventional design, associated with the probe, for sensing the liquid level in the sample containers is coupled to the controller 80 to control the depth to which the probe is moved.

Figure 3:
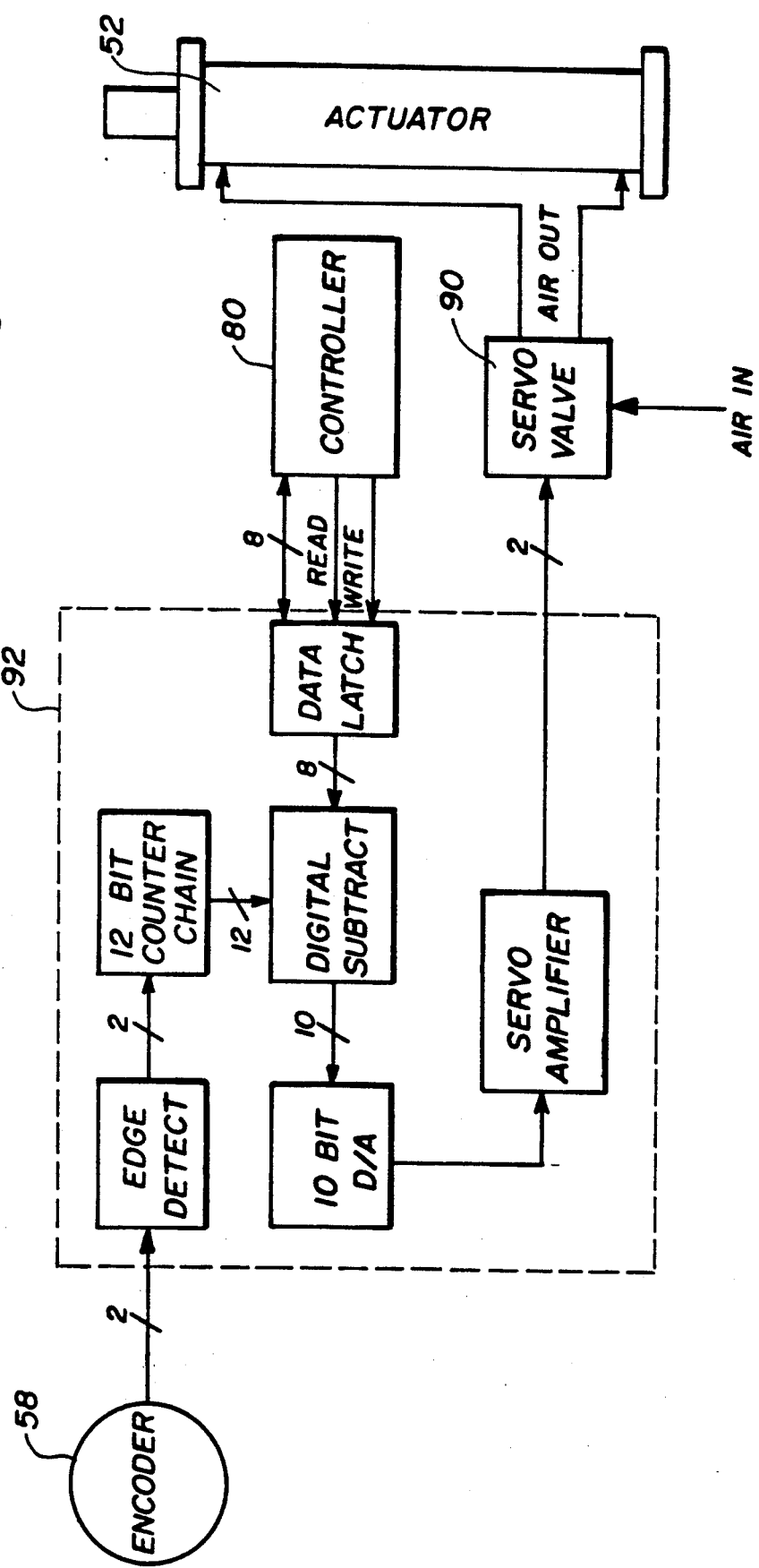
FIG. 3 is a block diagram of electronics used to control the apparatus of FIG. 1.

There may be seen in FIG. 3 a block diagram of the control system for the automatic sampler. The controller 80 may be any program controllable chip which stores information as to sample quantity, and is responsive to the probe level sense circuit 75 to provide input to the digital positioning board 92 one of the translators 40 or 42. For the sake of simplicity, the only translator described is the horizontal translator 42 although both function the same way. The horizontal encoder is seen as represented by the circle 58 and the bang-bang fluid motor or actuator by the block 52. The servo valve 90 controls the operation of air from a suitable air supply (not shown) to either end of the actuator 52. The control system may be seen as including the encoder 58, the actuator 52, the servo valve 90, the controller 80 and a digital positioning board 92 and converts a bang-bang pneumatic actuator to an actuator that is capable of precise position control. The positioning encoder 58 which might be any suitable rotary encoder such as a Lucas Ledex K3-DM-2500-5SE-4A provides outputs that are in quadrature. By sampling these outputs, the digital positioning board 92 is able to determine the direction of the actuator as well as the number of positions moved.

The servo valve 90 which may be any suitable servo valve, however, one manufactured by Atchley Controls, model 204PN is preferred. Such servo valve is a two stage jet-pipe servo valve. The first stage uses a torque driven jet-pipe which directs the airflow into one of two receiver orifices. Each orifice is connected to one end of a second stage spool which is directly connected to the output ports. When an actuator position is achieved, the valve is at null and the dual output ports reach an equal pressure balance.

The digital positioning board may, for example, be an Automation Plus, model DPC-256. The digital positioning board consists of a data latch, an edge detect circuit, a counter chain, digital subtractor, digital-to-analog converter and a servo amplifier. Two 8-bit tri-state latches let position programming and readback to occur on the same bus. A 4× edge detect circuit is used to react to every possible quadrature state, thereby eliminating positioning errors due to encoder shaft vibrations. A 12 bit up/down counter chain accepts counts from the edge detect circuit. The 12 bits from the counter chain are sent to a digital subtraction circuit. The 4 least significant bits are used for correction of any drift in the actuators position. The carry out on the digital subtraction circuit is used as a direction pointer. The 8 most significant bits are used in digital subtraction and drive the 10 bit digital-to-analog (D/A) converter. The 10 bit D/A converter works in conjunction with summing amplifiers and a servo amplifier. Corrections in position drift due to the expansion and contraction of air lines, compressibility of air, or offsets in the servo valve are automatically made by using the least significant bit of the D/A converter. The controller 80 provides position data and preferably is TTL compatible. When 8 bit parallel data is sent to the input data latch on the digital positioning board and a write pulse is generated, the actuator will move to a position proportional to the data at the input latch. For example, if the actuator has 6 inches of linear travel when at position 255, sending 128 decimal to the input data latch will move the actuator 3 inches back from its previous position of 255. Sending a read pulse to the output data latch will allow the data source to input position data and verify that the desired actuator position was achieved. Tight software control is not required to control and maintain the actuators movement. Once data and a write pulse are sent to the digital positioning board, the controller is free to perform other functions. The actuator 52 may be Bimba 02-3-DXDE, Bimba Pneu-Turn PT-017-078 Tolomatic BC-100-P-6.5. When air is applied to an input of an air cylinder, the actuator will move either in or out depending on what input the air was applied. Typically, a rack and pinion is mounted to the cylinder and the actuator. A rotary encoder is then mounted to the pinion gear. As the actuator 52 moves, the encoder rotates. This causes the encoder to generate pulses that are sent to the digital positioning board 92 as described.

OPERATION

The operation of the automatic sampling apparatus may be best understood by reference to FIGS. 1 and 2 in which sample, e.g. blood, collection tubes 16 with or without caps 17 are placed in carriers 14 and staged on the sample wheel 12. The sample wheel rotates in one direction only, to present each blood collection tube in sequence beneath the tube retainer 30 and probe 34. When the blood collection tube 16 is in the correct position, the controller commands sample wheel 12 motor 18 to stop beneath the sampling position. An electronic signal is sent to the X-axis rotary encoder by the positioning board 92 to sense for the relevant lateral position directly over the tube. Instantaneously a command signal is sent to the X-axis servo valve 90 from the positioning board to supply air to the correct port of the X-axis fluid motor to drive the probe 34 in a lateral direction toward the blood collection tubes. As the needle probe is moved by air toward the blood collection tube, the electronic rotary encoder, geared to the pinion driving rack 56 is forced to count by its rotating motion as it moves down the linear rack. When the rotary encoder has reached the correct position over the appropriate blood collection tube, it sends a signal to the servo valve via the positioning board to equalize air pressure in both ports (P1 & P2) of the X-axis fluid motor 42 thus stopping and locking its position directly over the appropriate blood collection tube 16. When the X-axis fluid motor has been locked into position by equalized air pressure, a command signal is sent to the second servo valve via the controller to supply fluid to the correct port of the Z-axis fluid motor to move the needle probe down through the (rubber) cap into the blood collection tube.

As the tip of the needle probe penetrates the rubber cap of the tube and exits the other side, and before entering the serum, a command signal is sent to the pump 72 to withdraw all fluid in the needle probe conduit back through the pump valve 70. The valve 70 is switched by the controller 80 to place conduit 68 in communication with atmospheric pressure to permit vacuum inside the tube above the serum level to equilibrate. All of this is accomplished almost instantaneously when the probe 34 enters the closed tube. Then the controller switches the valve back to the pump 72 and aspirates sample. To those skilled in the art, the relief of vacuum entrapped in a closed container above the fluid line is necessary to assure a precise aspiration of a desired sample quantity.

Before the needle probe enters the serum sample, the controller polls the level sense logic device 75 for the level of the serum sample. The level sense logic device sends a signal back to the controller 80 that the sample level has not been detected. Then the controller sends a signal to the servo valve 90 to supply fluid pressure to the Z-axis fluid motor to move the probe 34 down into the tube further. As the needle probe 34 moves further down into the tube, the level sense logic device is trying to detect a change in frequency. When the needle probe touches the fluid, a change in frequency is detected by the level sense logic device. It sends a signal back to the controller 80 that it has sensed sample and the controller signals the servo through the positioning board 92 to force the Z-axis fluid motor down an additional distance equivalent to 10 steps as determined by the electronic rotary encoder. This immerses the needle probe hole deep enough into the sample to permit evacuation of sample through the hole into the probe.

When sample has been aspirated, the controller 80 signals the servo 90 to supply fluid to the Z-axis port to move the probe up. Instantaneously a signal is sent by the controller to the Z-axis rotary encoder to count position as the needle probe is raised. When the needle reaches the appropriate position, the rotary encoder sends a command to the servo valve via the controller and positioning board to supply fluid to both ports of Z-axis fluid motor, thus locking the probe in the appropriate position. Upon locking the Z-axis fluid motor in the appropriate position the controller signals the servo valve to supply fluid to the correct X-axis fluid motor port to laterally move the needle probe. The controller signals the electronic encoder to count positions as the probe is moved to transfer the aspirated sample to a transfer vessel. Upon reaching the desired lateral position, the encoder 58 signals the servo valve 90 via the controller 80 to supply fluid to X-axis fluid motor ports stopping the needle probe over the transfer vessel. Then the controller 80 signals the Z-axis fluid motor port to move the probe down a designated number of steps as determined by the Z-axis rotary encoder. As the probe moves down, the rotary encoder counts the probe's relative position and signals the servo valve 90 via the controller 80 when the probe has reached the appropriate position. At the appropriate position or number of counts, the rotary encoder signals the servo valve 90 via the controller to supply fluid to both fluid motor ports to stop the probe 34. The controller 80 signals the pump to dispense the sample into the transfer vessel. After dispensing of the sample into the transfer vessel 22, the controller 80 signals the servo valve 90 and rotary encoder and moves the probe to a wash station 24 for needle probe tip cleaning.

As the probe is moved into the wash station 24 by the controller, the needle probe 34 is driven down into the drain at the appropriate position as designated by the controller and determined by the Z-axis rotary encoder. The controller signals the valve 70, 74 to switch to communicate the pump 72 with conduit 68 and the controller signals the pump 72 to flush the needle probe 34 via valve 74 with distilled water from wash 76. As the distilled water exits the probe 34, water is forced up around the outside of the probe tip as facilitated by the wash station geometry and then flows out of the wash station down into the liquid waste container 28. The controller 80 then raises the probe 34 in accordance with the previous teachings and is ready to move to another sample tube.

Although the closed tube sample method of this invention has been heretofore representatively illustrated, the same method is used for open tube sampling without piercing a rubber cap. Because piercing the rubber requires the greater force and optimized geometry and design of the needle probe, it is clear for those skilled in the art that open tube sampling is achieved using the same method and hardware with relative and less challenging ease.

In an alternative embodiment invention instead of a horizontal translator, a rotary translator may be used instead. In this case, as before, a Z-axis translator is mounted on a rotary translator operating in the horizontal plane. The advantage of a rotary translator is that in some situations it will result in space saving. Either one may be used with equal facility.

I claim:

1. In a sampling apparatus having a sample carrier adapted to move a plurality of sample containers into a sampling position, a lateral translator located to have a path of movement over the sampling position, a vertical translator mounted to be positioned laterally by the lateral translator, a sampling probe adapted to be positioned vertically by the vertical translator into and out of the sample containers, a liquid pump connected to the probe to aspirate sample from the sample containers, and controller means to actuate the translators and pump to effect such aspirations, the improvement wherein the translators are fluid driven actuators, the sample containers are upright, and at least one sample container is closed, and wherein the pump is connected by a conduit to the probe and which includes a valve positioned in the conduit and responsive to the controller means to open the conduit to atmospheric pressure immediately prior to sample aspiration to equilibrate the pressure in the closed sample container.

2. The sampling apparatus of claim 1 wherein each translator includes a fluid driven actuator connected to a position encoder and responsive to the position of the translator, servo valves to drive the actuator in opposite directions, and a digital positioning circuit responsive to the controller and the position encoder for controlling the servo valves to position the probe in accordance with a position designated by the controller.

3. In a sampling apparatus having a sample carrier adapted to move a plurality of sample containers into a sampling position, a lateral translator located to have a path of movement over the sampling position, a vertical translator mounted to be positioned laterally by the lateral translator, a sampling probe adapted to be positioned vertically by the vertical translator into and out of the sample containers, a liquid pump connected to the probe to aspirate sample from the sample containers, and controller means to actuate the translators and pump to effect such aspirations, the improvement wherein the translators are fluid driven actuators, the sample containers are upright, and at least on sample container is closed and which includes a retaining bracket for the sample containers positioned to limit their upward movement during probe withdrawal from the container, and wherein the pump is connected by a conduit to the probe and which includes a valve positioned in the conduit and responsive to the controller means to open the conduit to atmospheric pressure immediately prior to sample aspiration to equilibrate the pressure in the closed sample container.

4. The sampling apparatus of claim 3 wherein each translator includes a fluid driven actuator connected to a position encoder responsive to the position of the translator, servo valves to drive the actuator in opposite directions, and a digital positioning circuit responsive to the controller and the position encoder for controlling the servo valves to position the probe in accordance with a position designated by the controller.

5. In a sampling apparatus having a sample carrier adapted to move a plurality of sample containers into a sampling position, a lateral translator located to have a path of movement over the sampling position, a vertical translator mounted to be positioned laterally by the lateral translator, a sampling probe adapted to be positioned vertically by the vertical translator into and out of the sample containers, a liquid pump connected to the probe to aspirate sample from the sample containers, and controller means to actuate the translators and pump to effect such aspirations, the improvement wherein the translators are fluid driven actuators, the sample containers are upright, and at least one sample container is closed and which includes a retaining bracket for the sample containers positioned to limit their upward movement during probe withdrawal from the container, a transfer vessel located along the path of movement of the lateral translator, said controller means operating the lateral translator to position the probe over the transfer vessel, the vertical translator and pump operating to discharge aspirated sample into the transfer vessel, a wash receptacle located along the path of movement of the lateral translator, said controller means operating the lateral translator to position the probe over the wash receptacle, a source of wash liquid, the pump being coupled to the source, the vertical translator and pump operating to discharge wash liquid into the receptacle and to dip the probe into the receptacle to wash the probe, and the pump connected by a conduit to the probe, and a valve positioned in the conduit and responsive to the controller means to open the conduit to atmospheric pressure immediately prior to sample aspiration to equilibrate the pressure in the closed sample container.

6. The sampling apparatus of claim 5 wherein each translator includes a fluid driven actuator connected to a position encoder and responsive to the position of the translator, servo valves to drive the actuator in opposite directions, and a digital positioning circuit responsive to the controller and the position encoder for controlling the servo valves to position the probe in accordance with a position designated by the controller.

* * * * *